United States Patent
Jolly et al.

(10) Patent No.: US 9,689,010 B2
(45) Date of Patent: Jun. 27, 2017

(54) MICROBIAL-DERIVED CHONDROITIN SULFATE

(71) Applicants: Amano Enzyme USA., Ltd., Elgin, IL (US); Amano Enzyme, Inc., Naka-ku, Nagoya (JP)

(72) Inventors: James F. Jolly, Elgin, IL (US); Krzysztof Klimaszewski, Harwood Hts., IL (US); Yuji Nakanishi, Gifu (JP); Hirotaka Matsubara, Gifu (JP); Tetsuya Takahashi, Gifu (JP); Kyouichi Nishio, Gifu (JP)

(73) Assignees: AMANO ENZYME USA, LTD., Elgin, IL (US); AMANO ENZYME, INC., Nagoya (JP)

(*) Notice: Subject to any disclaimer, the term of this patent is extended or adjusted under 35 U.S.C. 154(b) by 1 day.

(21) Appl. No.: 14/793,947

(22) Filed: Jul. 8, 2015

(65) Prior Publication Data

US 2016/0024544 A1    Jan. 28, 2016

Related U.S. Application Data

(62) Division of application No. 12/477,492, filed on Jun. 3, 2009, now Pat. No. 9,109,243.

(60) Provisional application No. 61/129,084, filed on Jun. 4, 2008.

(51) Int. Cl.
| | | |
|---|---|---|
| *C08B 37/08* | (2006.01) | |
| *C12P 19/04* | (2006.01) | |
| *A61K 31/726* | (2006.01) | |
| *A61K 31/737* | (2006.01) | |
| *C08B 37/00* | (2006.01) | |
| *C12P 19/26* | (2006.01) | |
| *C08L 5/08* | (2006.01) | |

(52) U.S. Cl.
CPC ............ *C12P 19/04* (2013.01); *A61K 31/726* (2013.01); *A61K 31/737* (2013.01); *C08B 37/0069* (2013.01); *C08L 5/08* (2013.01); *C12P 19/26* (2013.01)

(58) Field of Classification Search
CPC .......... A61K 2236/333; A61K 2236/39; A61K 2236/53; A61K 39/0002; C08L 5/08
See application file for complete search history.

(56) References Cited

U.S. PATENT DOCUMENTS 9,109,243 B2    8/2015   Jolly et al.

FOREIGN PATENT DOCUMENTS

| EP | 1 304 338 A1 | 4/2003 |
| WO | WO 01/02597 A1 | 1/2001 |

OTHER PUBLICATIONS

International Search Report issued on Oct. 8, 2009 in application No. PCT/US2009/046089.
Ninomiya et al., "Molecular Clonging and Characterization of Chondroitin Polumerase from *Eschericha coli* Strain K4," *The Journal of Biological Chemistry*, vol. 277, No. 24, pp. 21567-21575, Jun. 14, 2002.
De Angelis et al., "Identification and Molecular Cloning of a Chondroitin Snythase from *Pasteurella multocida* Type F, " *The Journal of Biological Chemistry*, vol. 275, No. 31, pp. 24124-24129, Aug. 4, 2000.
Silbert et al., "Biosynthesis of Chondroitin/Dermatan Sulfate," *IUBMB Life*, vol. 54, No. 4, pp. 177-186, Oct. 1, 2002.
Reginster et al., "Symptom and Structure Modifying Properties of Chondroitin Sulfate in Osteoarthritis," *Mini-Reviews in Medicinal Chemistry*, vol. 7, pp. 1051-1061, 2007.
Davies et al., "Characterization and Purification of Glycosamioglycans from Crude Biological Samples," *J. Agric. Food Chem.*, vol. 56, pp. 343-348, 2008.
Sim et al., "Quantitative analysis of chondroitin sulfate in raw materials, ophthalmic solutions, soft capsules and liquid preparations," *Journal of Chromatography*, vol. 818, pp. 133-139, 2005.
Lidholt et al., "Biosynthesis of the *Escherichia coli* K4 Capsule Polysaccharide," The Journal of Biological Chemistry, vol. 272, No. 5, pp. 2682-2687, Jan. 31, 1997.
Office Action issued on Aug. 25, 2011 in U.S. Appl. No. 12/477,492 (U.S. Pat. No. 9,109,243).
Office Action issued on Dec. 13, 2011 in U.S. Appl. No. 12/477,492 (U.S. Pat. No. 9,109,243).
Office Action issued on Sep. 28, 2012 in U.S. Appl. No. 12/477,492 (U.S. Pat. No. 9,109,243).
Office Action issued on Jun. 2, 2014 in U.S. Appl. No. 12/477,492 (U.S. Pat. No. 9,109,243).
Office Action issued on Jan. 29, 2015 in U.S. Appl. No. 12/477,492 (U.S. Pat. No. 9,109,243).
Notice of Allowance issued on Apr. 17, 2015 in U.S. Appl. No. 12/477,492 (U.S. Pat. No. 9,109,243).

*Primary Examiner* — Robert C Hayes
(74) *Attorney, Agent, or Firm* — Foley & Lardner LLP

(57) ABSTRACT

Described is chondroitin sulfate obtained from microbial sources, and related compositions and methods.

6 Claims, 8 Drawing Sheets

*Bacillus natto Naruse Strain*

MICROBIAL-DERIVED CHONDROITIN SULFATE

CROSS-REFERENCE TO RELATED APPLICATION

This application claims the benefit of priority under 35 U.S.C. §119(e) to U.S. Provisional Application No. 61/129,084, filed Jun. 4, 2008, the entire contents of which are incorporated herein by reference in their entirety.

FIELD OF INVENTION

Described herein is chondrotin sulfate obtained by microbial fermentation, such as from *Bacillus natto*, and related compositions and methods.

BACKGROUND

Osteoarthritis (OA) is the most common musculoskeletal disease and it affects about 10% of the world's population aged 60 and older. Buckwalter, J. A. and Martin, J. A. *Adv. Drug Deliv. Rev.*, 58, 150 (2006). OA affects the entire joint and is characterized by a loss of cartilage. Conventional OA treatment consists of nonsteroidal anti-inflammatory drugs (NSAIDs) and analgesics. Reviewed in, e.g., Reginster, J-Y., et al. *Mini-Reviews in Medicinal Chemistry*, 7, 1051-1061 (2007). However, many of these drugs can cause serious side effects and therefore strategies have been developed for using chondroitin sulfate as a means for treating OA. Chondroitin sulfate (CS) is widely used to treat OA. See, e.g., Reginster et al., "Symptom and Structure Modifying Properties of Chondroitin Sulfate in Osteoarthritis," *Mini-Reviews in Med. Chem.*, 7: 1051-61 (2007). CS is classified as a symptomatic slow acting drug in osteoarthritis (SYSADOAs), acting after a few weeks time, as compared to analgesics and NSAIDs, which act within a few hours.

Chondroitin sulfate (CS) is a major component of the extracellular matrix, and is found in animal cartilage. CS is a sulfated glycosaminoglycan (GAG) consisting of repeating units of alternating glucuronic acid and N-acetyl-galactosamine that contains sulfate groups at one or more positions on the N-acetyl-galactosamine units, such as the 4 position (CS A), 6 position (CS C), 2 position (CS D) or the 4 and 6 positions (CS E). While the size of CS varies, typical CS molecules have a size of about 20,000 to 50,000 daltons. Current sources of CS include cartilage from various animals, such as pigs (ear and nose), cows (trachea), sharks, fish and birds.

SUMMARY OF THE INVENTION

In accordance with some embodiments, there is provided methods for producing a chondroitin sulfate-like compound, comprising (a) culturing a microbial culture under conditions suitable for chondroitin sulfate production; and (b) obtaining chondroitin sulfate from the culture. In some embodiments, the microbial culture comprises a bacterium or a fungus, such as a naturally occurring bacterium or a naturally occurring fungus.

In some embodiments, the bacterium is from a genus selected from the group consisting of *Corynebacterium, Microbacterium, Micrococcus, Monascus, Streptomycetes, Escherichia, Bacillus* and *Lactobacillus*, including *Bacillus natto*, such as a strain of *Bacillus natto* selected from the group consisting of the Naruse strain, the Miura strain and the Takahashi strain. In some embodiments, the bacterial culture comprises *natto*.

In some embodiments, the fungus is from a genus selected from the group consisting of *Aspergillus, Endomycopsella, Endomycopsis, Hansenula, Hasegawaea, Penicillium, Pichia, Monascus, Candida, Debaryomyces, Eurotium, Galactomycetes, Geotrichum, Rhodotorula, Saccharomyces, Trichoderma, Kluveromyces, Schizosaccharomyces, Streptomyces, Talaromyces. Torulopsis, Yamadazyma, Yarrowia, Zygosaccharomyces, Mucor, Mortierella, Rhizomucor, Rhizopus, Cryptococcus, Dipodascus*, and *Trichosporon*.

In some embodiments, the culturing comprises incubating the microbial culture in nutrient broth at 37° C. In some embodiments, the culturing comprises incubating the microbial culture in culture medium at 30° C. In some embodiments, the culturing comprises two stages: a first stage comprising culturing in a pre-culture medium and a second stage comprising culturing in a main culture medium.

In some embodiments, the obtaining comprises a method selected from the group consisting of centrifugation to remove microbial cells, filtration, chromatography, and alcohol precipitation.

In accordance with other embodiments, there is provided an isolated chondroitin sulfate-like compound produced by the methods described hereinabove and below. In some embodiments, the isolated chondroitin sulfate-like compound is chondroitin sulfate. In some embodiments, the isolated chondroitin sulfate-like compound comprises N-acetyl-galactosamine groups having a sulfate group at the 4 position and N-acetyl-galactosamine groups having a sulfate group at the 6 position.

In accordance with other embodiments, there is provided a composition comprising an isolated chondroitin sulfate-like compound produced by the methods described herein above and below. In some embodiments, the composition is a pharmaceutical composition, nutraceutical composition, or food product.

In accordance with other embodiments, there is provided an isolated microbial-derived chondroitin sulfate-like compound. In some embodiments, the chondroitin sulfate-like compound comprises N-acetyl-galactosamine groups having a sulfate group at the 4 position and N-acetyl-galactosamine groups having a sulfate group at the 6 position, wherein the ratio of disaccharides with sulfate at the 4 position (4S) to disaccharides with sulfate at the 6 position (6S) is greater than 1, or is less than 1. In some embodiments, the chondroitin sulfate-like compound has a molecular weight selected from (i) about 300 to about 3,000 daltons; (ii) about 1,000 to about 10,000 daltons; (iii) about 500 to about 15,000 daltons; and (iv) about 1,000 to about 20,000 daltons; (iv) about 1,000 to about 25,000 daltons; (iv) about 5,000 to about 35,000 daltons. In some embodiments, the microbial-derived chondroitin sulfate-like compound is chondroitin sulfate.

In accordance with other embodiments, there is provided a method for the treatment or prevention of osteoarthritis, or for the maintenance of musculoskeletal health, comprising administering to a patient in need thereof a therapeutically effective amount of a chondroitin sulfate-like compound produced by the methods described herein above and below.

DETAILED DESCRIPTION

The present invention relates to the discovery that CS, or a CS-like compound, can be obtained from microbial sources, including bacterial sources, such as *Bacillus natto*, and fungal sources. This is an important discovery because current methods of obtaining CS from animal sources may not be able to satisfy the increasing demand for CS. For example, it would take millions of animals to obtain enough CS to satisfy a large commercial market, such as Japan. Additionally, CS from microbial sources avoids the potential of contamination with animal viruses and prions that may be associated with CS from current animal sources.

Thus, in accordance with some aspects, the present invention provides microbial-derived CS or CS-like compound that can be used instead of currently available animal-derived CS. Compositions comprising microbial-derived CS or CS-like compound, and methods of making and using it, also are provided. The microbial-derived CS or CS-like compound described herein are free of animal contaminants, including mammalian contaminants, such as mammalian proteins, viruses and prions, that may be present in CS obtained from cows or pigs.

All technical terms used herein are terms commonly used in biochemistry, molecular biology and agriculture, and will readily be understood by one of ordinary skill in the art to which this invention belongs.

As used herein, the singular forms "a," "an," and "the" designate both the singular and the plural, unless expressly stated to designate the singular only.

As used herein, "chondroitin sulfate" denotes a sulfated glycosaminoglycan (GAG) consisting of repeating units of alternating glucuronic acid and N-acetyl-galactosamine that contains sulfate groups at one or more positions on the N-acetyl-galactosamine units.

Figure 5:
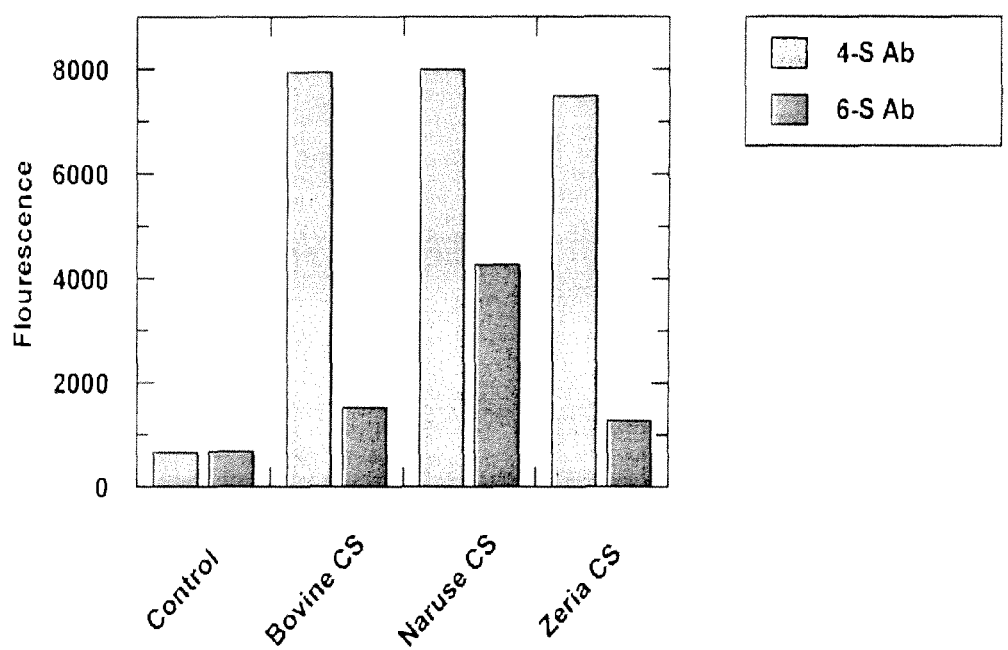
FIG. 5 shows ELISA analysis of CS digestion products from bovine, *Bacillus natto* Naruse strain and porcine CS.

As used herein, "chondroitin sulfate-like compound" denotes a compound that exhibits chondroitin sulfate activity in the dimethylene blue assay (DMMBA) described herein and/or can be digested by chondroitinase and detected by antibodies to the 4S and 6S dissacharides of CS, as illustrated in FIG. 5. In some embodiments, the chondroitin sulfate-like compound is chondroitin sulfate. In some embodiments, the CS-like compound includes N-acetyl-galactosamine groups that contain sulfate groups at one or more positions, such as at the 4, 6, 2 or the 4 and 6 positions. In some embodiments, the CS-like compound additionally or alternatively includes glucuronic acid groups. In some embodiments, the CS-like compound includes repeating units of alternating glucuronic acid and N-acetyl-galactosamine groups that contains sulfate groups at one or more positions, such as at the 4, 6, 2 or the 4 and 6 positions.

In some embodiments, the CS-like compound has a size consistent with animal-derived chondroitin sulfate. In other embodiments the CS-like compound has a size different from animal-derived chondroitin sulfate. In some embodiments, the CS-like compound has a 4S:6S ratio similar to that of an animal-derived chondroitin sulfate. In other embodiments, the CS-like compound has a 4S:6S ratio different from that of an animal-derived chondroitin sulfate.

While animal-derived CS compounds typically have a size between 20,000 and 50,000 daltons, microbial-derived CS-like compounds typically exhibit a size below 20,000 daltons, as illustrated in Table 2 below, although some microbial-derived CS-like compounds exhibit a size above 20,000 daltons, as also illustrated in Table 2. Thus, microbial-derived CS-like compounds may have a size between 300 and 50,000 daltons, or greater. In one embodiment, a microbial-derived CS-like compound has a molecular weight between 300 and 3,000 daltons. In another embodiment, a microbial-derived CS-like compound has a molecular weight between 1,000 and 10,000 daltons. In an other embodiment, a microbial-derived CS-like compound has a molecular weight between 500 and 15,000 daltons. In another embodiment, a microbial-derived CS-like compound has a molecular weight between 1,000 and 20,000 daltons. In another embodiment, a microbial-derived CS-like compound has a molecular weight between 1,000 and 25,000 daltons. In another embodiment, a microbial-derived CS-like compound has a molecular weight between 5,000 and 35,000 daltons. In another embodiment, a microbial-derived CS-like compound has a molecular weight up to 50,000 daltons, or greater.

The ratio of N-acetyl-galactosamine groups with sulfates at the 4 position (4S) to groups with sulfates at the 6 position (6S) (for example, as determined by analyzing the disaccharides resulting from chondroitinase digestion) varies with the source of the chondroitin sulfate. For example, shark chondroitin sulfate has more 6S than 4S, while bovine and porcine chondroitin sulfate have more 4S than 6S. Microbial-derived CS-like compounds exhibit a broad range of 4S:6S ratios, as illustrated in Table 2 below. This variation may be due in part to the particular microbial production strain and/or to the culture conditions. In one embodiment, a microbial-derived CS-like compound has a 4S:6S ratio of less than 1. In another embodiment, a microbial-derived CS-like compound has a 4S:6S ratio of greater than 1. In another embodiment, a microbial-derived CS-like compound has a 4S:6S ratio of between 1 and 6. In another embodiment, a microbial-derived CS-like compound has a 4S:6S ratio of greater than 6.

Microbial Sources

A variety of microorganisms can be cultured for CS or CS-like compound production. In some embodiments, the microorganisms are naturally occurring microorganisms, such as microorganisms that have not been genetically engineered or recombinantly transformed to produce CS or CS-like compound. Exemplary microorganisms include but are not limited to bacteria and fungi.

Figure 4:
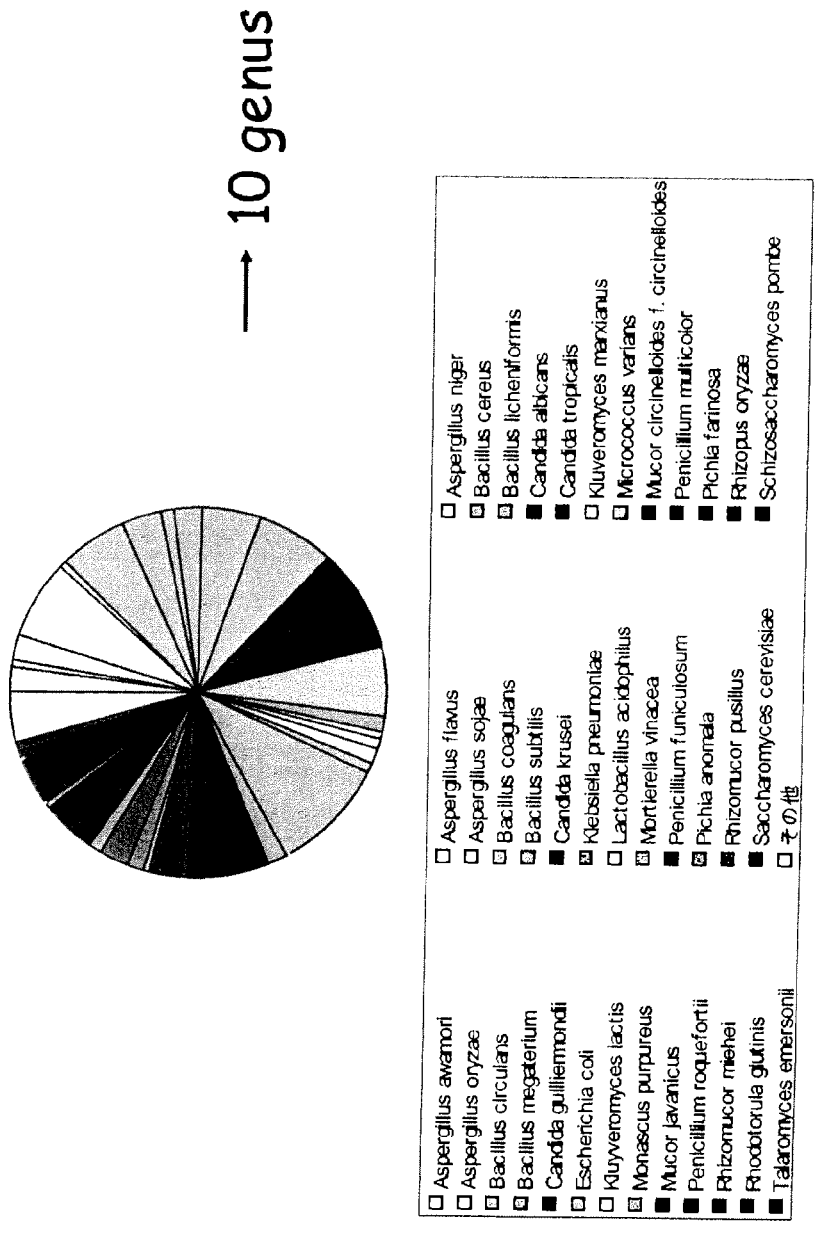
FIG. 4 shows the microbial strains selected from a broth library screening.

Illustrative bacteria include but are not limited to phyla Actinobacteria (e.g. genera *Corynebacterium, Microbacterium, Micrococcus, Monascus,* and *Streptomycetes*), Proteobacteria (e.g. genera *Escherichia*), and Firmicutes (e.g. genera *Bacillus* and *Lactobacillus*). Suitable bacteria include those listed in Table 3 and FIG. 4. Suitable bacteria are well-known in the art and publicly available from, e.g., a commercial supplier, food product, or natural source, such as soil.

One microbial source of particular interest is *Bacillus natto*, which is a sub-species of *Bacillus subtilis*. As discussed in more detail in the examples below, to date three different strains of *Bacillus subtilis* var. *natto* have been identified as producers of CS-like compound: the Naruse, Miura and Takahashi strains.

*Bacillus natto* currently is used in the commercial production of the Japanese food *natto* and the similar Korean food cheonggukjang. Any source of *Bacillus natto* can be used in the methods described herein, such as *Bacillus natto* from a commercial supplier or natural source, such as soil. Alternatively, the *natto* food product, which contains *Bacillus natto*, can be used as a source of *Bacillus natto*.

Other *Bacillus* strains also have been found to produce CS or CS-like compound, as illustrated in the examples below.

Illustrative fungi include but are not limited to phyla Deuteromycota (e.g. genera *Aspergillus*), Ascomycota (e.g. genera *Endomycopsis, Hansenula, Hasegawaea, Penicillium, Pichia, Monascus, Candida, Debaryomyces, Eurotium, Galactomycetes, Geotrichum, Saccharomyces, Trichoderma, Kluveromyces, Schizosaccharomyces, Talaromyces. Torulopsis, Yamadazyma, Yarrowia*, and *Zygosaccharomyces*), Zygomycota (e.g. genera *Mucor, Mortierella, Rhizomucor*, and *Rhizopus*), Basidiomycota (e.g. genera *Cryptococcus, Dipodascus*, and *Trichosporon*). Suitable fungi include those listed in Table 4 and FIG. 4. Fungi are well-known in the art and publicly available from, e.g., a commercial supplier, food product, or natural source, such as soil.

Microbial strains that produce CS or CS-like compounds can be identified by following the methods outlined in the examples below.

Production Methods

Microbial-derived CS or CS-like compounds can be obtained by culturing any microorganism that produces CS or CS-like compound, including microorganisms that have not been genetically engineered or recombinantly transformed to produce CS or CS-like compound, such as a naturally occurring CS-producing strain of *Bacillus natto*.

The microorganism can be cultured under standard conditions. For example, bacterial cultures of *Bacillus natto* may be grown in a nutrient broth at 37° C. overnight and then the overnight culture may be centrifuged to separate bacterial cells from CS or CS-like compound in the broth. Alternatively, a sample of *natto* food product, such as a sample of a commercial preparation of *natto*, may be cultured under the same or similar conditions to obtain CS or CS-like compound. Fungal microorganisms likewise can be cultured under standard conditions including tank or liquid fermentation or solid state fermentation, such as fermentation on solid wheat bran.

Suitable culture media can be selected by the skilled practitioner based on the microorganism being cultured. Any type of medium can be used, provided that a CS-producing microorganism can be grown therein. For example, a medium to be used may contain carbon sources such as glucose, sucrose, gentiobiose, soluble starch, glycerol, dextrin, molasses and organic acids; nitrogen sources such as ammonium sulfate, ammonium carbonate, ammonium phosphate, ammonium acetate, peptone, yeast extract, corn steep liquor, casein hydrolysate, wheat bran and meat extract; and inorganic salts such as potassium salts, magnesium salts, sodium salts, phosphates, manganese salts, iron salts and zinc salts.

In some embodiments, an inducer can be added to the medium in order to enhance production of the CS-like compound. Examples of suitable inducers include saccharides, such as gentose (e.g., Gentose #80, Nihon Shokuhin Kako), gentiobiose and gentio-oligosaccharide (e.g., Gentio-oligosaccharide, Wako Pure Chemicals). The skilled practitioner can determine a suitable amount of inducer to be added depending on the strain and/or culture conditions. Exemplary amounts include from 0.01 to 5%.

In some embodiments, the pH of the medium is adjusted to a level of approximately from 3 to 8, including from about 5 to 6. In some embodiments, the culturing is carried out under aerobic conditions at a culturing temperature of generally from about 10 to 50° C., such as at about 30° C., or about 37°. In some embodiments, the culturing is carried out for a period of from 1 to 15 days, including from 3 to 7 days. In general, any culturing method can be used that permits the production of CS-like compound, and the skilled practitioner will be able to select appropriate culture conditions depending on the microorganisms to be cultured and the culturing method.

In some embodiments, cultivation comprises two stages, involving different media, such as a pre-culture media and main culture media, as illustrated in the examples below.

As noted above, suitable culture conditions can be selected by the skilled practitioner based on the microorganism being cultured. For example, as shown in Table 1 in Example 6 below, 10 ml of a pre-culture medium can be added to a culture tube that is held at 30° C. for 1-2 days with rotation of 200 rpm. Then the microorganism can be transferred to a suitable flask (such as a 100 ml or 300 ml flask) with 50 ml culture medium, and cultured at 30° C. for 3-5 days with rotation of 200 rpm. These conditions are illustrative only.

Additional purification steps may optionally be performed to obtain isolated CS or CS-like compound, such as chromatography, including ion exchange chromatography, and/or filtration, including gel filtration, ultrafiltration, and alcohol precipitation, such as differential alcohol precipitation or ethanol precipitation in the presence of salt.

Large scale fermentation procedures known in the art can be used to produce commercial quantities of microbial-derived CS or CS-like compound. Commercial batches may optionally be purified, such as by ultrafiltration, and isolated CS or CS-like compound can be obtained, for example, by spray-drying the purified culture broth Alternatively, ethanol precipitation followed by vacuum drying will yield solid microbial-derived CS or CS-like compound.

Microbial strains that are particularly efficient at producing CS or CS-like compound can be developed by strain development procedures that are known in the art, e.g., by multiple rounds of mutagenesis and selection of CS-secreting strains (using for example the DMMB assay described below). In some embodiments, the mutagenesis does not involve genetically engineering or recombinantly transforming strains to produce CS or CS-like compound.

Analysis and Characterization

CS content can be quantified and analyzed by any known method in the art. For example, CS can be detected and analyzed using various dye assays, chromatographic tools, and electrophoretic techniques, including the chondroitinase treatment and HPLC and/or ELISA methodology described below.

For example, numerous dye assays are known in the art that may be used for detecting and quantifying glycosaminoglycans. While in no way limiting the present invention, suitable dye assays include the dimethylmethylene blue assay, the toluidine blue assay, and the Alcian blue assay. One suitable dimethylmethylene blue assay is illustrated in Example 1 below.

Various chromatography techniques may be used for quantifying and characterizing CS content and composition. For example, and in no way limiting the invention, suitable chromatography techniques include high performance liquid chromatography (HPLC), ion exchange chromatography, and size exclusion chromatography. ELISA methodologies also can be used, as illustrated in Example 8 below. In general, ELISA method can be used to characterize samples that are less concentrated and not extensively purified. Suitable methodologies are illustrated in the examples below.

Electrophoretic techniques also may be used to analyze CS. For example, fluorophore-assisted carbohydrate electrophoresis (FACE) may be used to evaluate the degree and location of sulfation on the GAG chain.

As noted above and illustrated in Example 5 below, HPLC is used to analyze CS from animal sources. Preliminary results indicate that bacteria-derived CS or CS-like compound yields an HPLC pattern that is similar to that of CS from animal sources. Alternatively, ELISA methodologies can be used, as illustrated in Example 8.

As an alternative, CS can be hydrolyzed with acid and the resulting sugar components can be determined by HPLC. Because acid hydrolysis is likely to remove the sulfate groups, the sulfate content can be determined by determining the sulfur content of CS, using methods that are known in the art.

Products

A microbial-derived CS or CS-like compound described herein can be used in any compositions or methods where animal-derived CS is used, and in any compositions or methods where CS activity is desirable. For example, microbial-derived CS or CS-like compound can be formulated in a pharmaceutical composition or nutraceutical composition further comprising, for example, pharmaceutically or nutraceutically acceptable carriers and/or diluents. In some embodiments, the pharmaceutical or nutraceutical compositions are prepared in unit dosage forms comprising any suitable dosage of the CS or CS-like compound. A microbial-derived CS or CS-like compound also can be manufactured as a food additive and added to any food product.

Methods

A microbial-derived CS or CS-like compound can be used in therapeutic or prophylactic methods, such as in methods for the treatment or prevention of osteoarthritis and/or for the maintenance of musculoskeletal health. Such methods may comprise administering a therapeutically effective amount of microbial-derived CS or CS-like compound to a patient in need thereof, wherein such a patient can be any mammal, including humans, suffering from or at risk of developing osteoarthritis, or desiring to maintain musculoskeletal health using CS. As used herein, "therapeutically effective amount" means that amount that provides the specific response for which the CS is administered. It is emphasized that a therapeutically effective amount will not always be effective in treating the conditions/diseases described herein, even though such dosage is deemed to be a therapeutically effective amount by those of skill in the art. Those skilled in the art can adjust such amounts in accordance with standard practices as needed to treat a specific subject and/or condition/disease.

The following examples are illustrative only, and in no respect limit the invention. Other aspects of the invention will be apparent to those skilled in the art to which the invention pertains.

Example 1. Dimethylmethylene Blue (DMMB) Assay for CS

Many versions of the DMMB assay exist. The DMMB assay described herein has good specificity for CS, and does not detect keratan sulfate, dermatin sulfate, hyaluronic acid or other polymers such as protein or DNA, due to the low pH and high salt concentration in the assay. Thus, the assay can be utilized to determine the amount of CS in crude samples. See, e.g., Farndale et al., "Improved Quantization and Discrimination of Sulphated Glycosaminoglycans by Use of Dimethylmethylene Blue," *Biochemica Et Biophysical Acta* 883 173-77. (1986); Davies et al., "Characterization and Purificatiion of Glycosaminoglycans from Crude Biological Samples," *J. Agric. Food Chem.* 56: 343-48 (2008).

Materials:

Dimethylmethylene blue (DMMB) hydrochloride can be purchased from BioChemica International (Melbourne, Fla.). (An alternative source is 1,9-dimethylmethylene blue hydrochloride from Polysciences, Inc. (Warrington, Pa.)). Sodium chloride and glycine can be purchased from Sigma. Hydrochloric acid (w/w, 36.5-38%) can be purchased from Fisher Scientific. Chondroitin sulfate A sodium salt (from bovine trachea) can be purchased from Sigma.

Preparation of DMMB:

The dye can be prepared by dissolving dimethylmethylene blue (4 mg) in a solution containing glycine (0.76 g), NaCl (0.5925 g), and 0.1 M HCl (23.75 mL) and deionized (DI) water (226.25 mL) to a total volume of 250 mL. The solution is stirred until the reagents are dissolved. The pH of the dye solution is pH 3.0 and absorbance ($A_{525}$) is about 0.300±0.06. The dye is stable for 3 months while stored in a brown bottle at room temperature. A 0.1 M HCl solution is prepared by taking stock HCl (w/w, 36.5-38%, ~12M) (0.42 mL) and dissolving in deionized water (49.58 mL).

DMMB Procedure:

Sample or Standard (40 μL) is added to a disposable 1 mL spectrophotometer cuvette containing dimethylmethylene blue dye solution (1 mL). The solution is mixed by inverting the parafilm covered cuvette 5 times. The absorbance at 525 nm ($A_{525}$) is read within the first few seconds after stabilization, which happens within 10 seconds. A calibration curve is prepared using chondroitin sulfate A sodium salt from bovine trachea (Sigma) as the standard. The assay has a linear range of 0-4 μg/ml. The total time for the analysis of one sample should be <1 minute from beginning to end to avoid inaccurate results due to precipitation of the dye.

When assaying crude samples, samples can be assayed without dilution, unless the samples are known to contain high levels of CS. If the absorbance reading is high (e.g., $A_{525}$~0.7) dilutions can be used.

Example 2. Isolation of Bacteria-Derived CS

Sterile nutrient broth (DIFCO), 100 ml, is inoculated with a small portion (about 1 g) of *natto* obtained from a grocery store. The culture is incubated at 37° C. with shaking (200 RPM) overnight (about 14 hours). The culture is centrifuged at 3000 g for 30 minutes to pellet bacteria cells. The clear culture is removed and assayed for the presence of CS-like compound by the DMMB assay described above. The culture media is determined to contain 0.2 g CS/L (or CS-like compound/L).

Example 3. Determination of CS Size by Size Exclusion Chromatography

The size of CS is measured by size exclusion chromatography using a Superdex 200 10/300GL column and an Akta Explorer FPLC chromatography system (GE Healthcare). Sample (0.5 ml) is injected on the column and the column is run at 0.1 ml/min in 10 mM Tris HCl (pH 8.0)

buffer. Protein is monitored at O.D. 280 nm and CS is monitored at O.D. 215 nm. Fractions are collected (1 ml) and assayed for the presence of CS by the DMMB assay. The molecular size is estimated by a pre-calibration of the column with standard proteins of known size (GE Healthcare).

Figure 1:
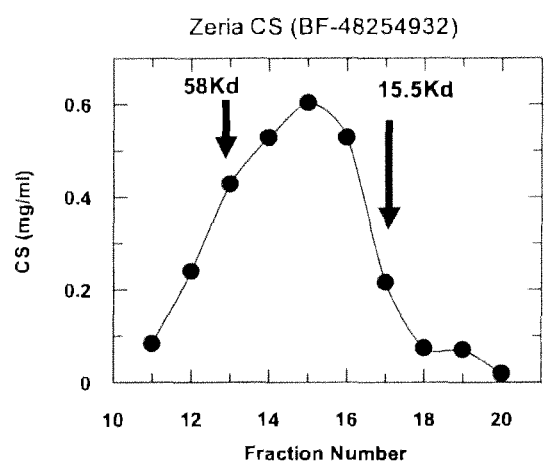
FIG. 1 shows the results of an analysis of the size distribution of porcine CS by size exclusion chromatography, plotting CS content as compared to fraction number.

FIG. 1 shows the results of an analysis of the size distribution of porcine CS by size exclusion chromatography, plotting CS content as compared to fraction number. The molecular weight markers are an extrapolation from a calibration profile and linear regression line which relates elution volume (or fraction number) to molecular weight in kilodaltons (Kd).

Figure 2:
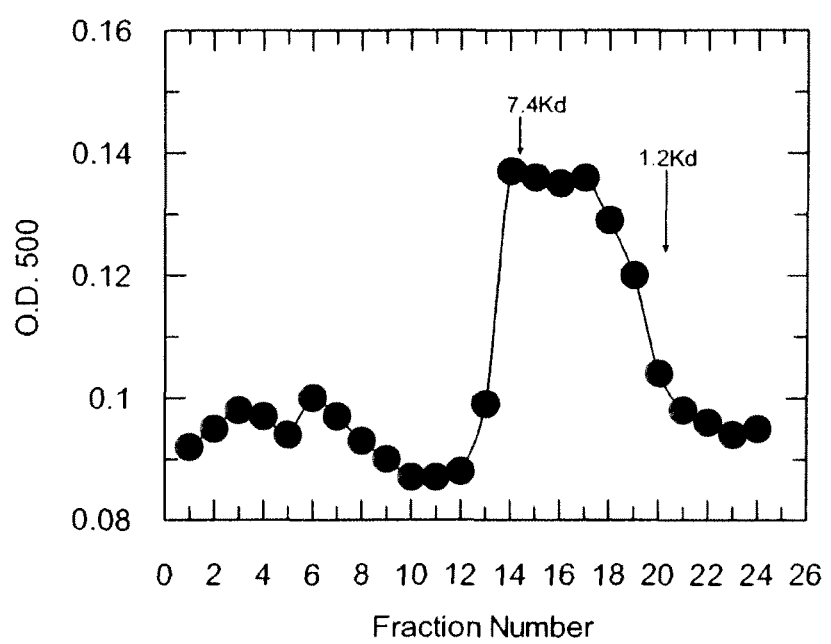
FIG. 2 shows the results of an analysis of the size distribution of bacteria-derived CS by size exclusion chromatography, plotting CS content as compared to fraction number.

FIG. 2 shows the results of an analysis of the size distribution of bacteria-derived CS (obtained from the Naruse strain of *Bacillus natto* as described in Example 7 below) by size exclusion chromatography, plotting CS content as compared to fraction number. The results indicate that the bacteria-derived CS (obtained from the Naruse strain of *Bacillus natto*) has a molecular weight of about 10 Kd or less.

Example 4. Characterization of CS by HPLC

Animal-derived CS can be characterized by a process that includes chondroitinase digestion and HPLC analysis of the resulting disaccharide units. HPLC separates the disaccharide units of the polymer by sulfate content: disaccharides that contain no sulfate are eluted first, followed by disaccharides that contain sulfate in the 4 position of N-acetyl-galactosamine (GalNac) and then disaccharides that contain sulfate in the 6 position of GalNac. See, e.g., Sim et al., "Quantitative analysis of chondrotin sulfate in raw materials, ophthalmic solutions, soft capsules and liquid preparations," *J. Chromatog.* 818: 133-39 (2005).

For HPLC analysis, the CS polymer is first hydrolyzed (digested) by chondroitinase enzymes (available from Sigma or other vendors) into disaccharide units. The resulting mixture is applied to a suitable HPLC column, such as a Phenomenex Synergi 4u Polar-RP 80A column, and eluted with a gradient of 1 mM tetrabutylammonium bisulfate to 50:50 1 mM tetrabutyammonium bisulfate: acetonitrile. The flow rate is 1 ml/min and O.D. is monitored at 240 nm. The column is calibrated with standard sulfated disaccharides (also available from Sigma).

FIG. 3 shows typical HPLC analysis of CS from bovine trachea (A), shark cartilage (B), and porcine trachea (C), and from the Naruse strain of *Bacillus natto* (D). As the data show, the ratio of disaccharides with sulfates at the 4 position (4S) to disaccharides with sulfates at the 6 position (6S) varies with the animal source of the CS. For example, shark CS has more 6S than 4S, while bovine and porcine CS have more 4S than 6S. Moreover, porcine CS has reproducibly higher amounts of 6S as compared to bovine CS. The microbial-derived CS has similar 4S and 6S levels. The 4S:6S ratio also may vary with the age of the animal or specific tissue source of the CS, and, for microbial-derived CS, with the culture conditions.

Example 5. Ion Exchange Chromatography

Porcine or microbial-derived CS, such as bacteria-derived, is applied to a suitable ion exchange chromatography column, such as a DEAE FF 16/10 column (GE Healthcare) and run on a Akta Explorer FPLC system (GE Healthcare). The flow rate is set at 1 ml/min and the column is eluted with a linear buffer of 0-1 M NaCl in 10 mM Tris HCl (pH 8.0) buffer. The CS is monitored at O.D. 215 nm, and 2 ml fractions are collected and assayed for CS by the DMMB assay described above. The porcine CS binds to the column tightly, eluting only at 1M salt. The bacteria-derived CS binds to the column less tightly, eluting at about 0.5-0.7 M NaCl. While not wanting to be bound by any theory, these results suggest that bacteria-derived CS contains fewer sulfate groups than porcine CS.

Example 6. Broth Library Screening of Strains Producing CS by DMMB Assay

Microbial strains that produce CS-like compound can be identified by the following process, which is illustrative only. Candidate strains are cultured under conditions suitable for production of CS or CS-like compound, as illustrated in Table 1 below, which depicts conditions for a two-stage production cultivation.

TABLE 1

| Cultivation of Selected Strains | | |
|---|---|---|
| Name | Gentose pre-culture | Main culture |
| Penicillium multicolor | 8.3% B-ohgi medium: | Sun-grain medium |
| Rhizopus oryzae | 8.3% wheat bran | (pH 6.5): |
| Rhizopus oryzae | (liquid culture) | 1.5% LustergenFK |
| Mucor javanicus | 10 ml/culture tube | (soluble starch) |
| Mucor circinelloides f. circinelloides | 30° C. 200 rpm 2 days | 0.3% MeastPIG (yeast extract) |
| | | 0.3% $KH_2PO_4$ |
| | | 0.1% $MgSO_4 \cdot 7H_2O$ |
| Mucor javanicus | | 1.5% Sun-grain |
| Rhizomucor miehei | | (whiskey fermentation residue) |
| Rhizomucor miehei | | 50 ml/300 mlΔflask |
| Monascus purpureus | | 30° C. 200 rpm 5 days |
| Saccharomyces cerevisiae | | |
| Mucor javanicus | | |
| Penicillium funiculosum | 8.3% B-ohgi medium 10 ml/culture tube | 5% wheat bran: 5 g wheat bran/1.5 mL |

TABLE 1-continued

Cultivation of Selected Strains

| Name | Gentose pre-culture | Main culture |
|---|---|---|
| Penicillium roquefortii | | 30° 200 rpm 2 days | 5% wheat bran/100 mlΔflask (SSF) 30° C. 5 days |
| Rhizomucor pusillus | | |
| Monascus purpureus | | |
| Aspergillus oryzae BB-1-84-38 | | |
| Penicillium camembertii | | |
| Aspergillus niger | − | GPmedium (pH 5.7): 2.0% glucose | DGL screening medium 50 ml/300 mlΔflask 30° C. 200 rpm 5 days |
| Rhizopus oryzae | − | 0.5% Bacto peptone |
| Rhizopus oryzae | − | (DIFCO) |
| Mucor javanicus | − | 0.2% Yeast Extract |
| Monascus purpureus | − | 0.05% MgSO$_4$•7H$_2$O 0.1% KH$_2$PO$_4$ |
| Monascus purpureus | − | 10 ml/culture tube 30° C. 200 rpm 2 days |
| Schizosaccharomyces pombe | − | |
| Candida tropicalis | − | |
| Candida tropicalis | − | |
| Saccharomyces cerevisiae | − | |
| Candida albicans | − | |
| Saccharomyces cerevisiae | − | |
| Saccharomyces cerevisiae | − | |
| Aspergillus oryzae | + | |
| Aspergillus niger | + | |
| Aspergillus awamori | + | |
| Penicillium multicolor | + | |
| Rhizopus oryzae | + | |
| Rhizomucor pusillus | + | |
| Rhizomucor miehei | + | |
| Rhizomucor miehei | + | |
| Escherichia coli | − | Tryptic soy broth (DIFCO) (pH 7.3 ± 0.2 (25° C.)): | Bacteria screening medium (pH 7): |
| Bacillus licheniformis | − | 3% Tryptic soy broth | 1% Polypeptone |
| Escherichia coli | − | (DIFCO) | 0.25% yeast extract |
| Escherichia coli | − | 10 ml/culture tube | (DIFCO) |
| Bacillus licheniformis 501SMN11-MCI12 | − | 30° C. 200 rpm 1 day | 0.10% (NH$_4$)$_2$SO$_4$ 0.05% KH$_2$PO$_4$ 0.025% MgSO$_4$•7H$_2$O |
| Bacillus circulans | − | | 0.0001% CaCl$_2$•2H$_2$O (optionally, 0.5% |
| Bacillus subtilis | + | | gentiooligosaccharide) |
| Escherichia coli | + | | 50 ml/300 mlΔflask |
| Bacillus licheniformis | + | | 30° C. 200 rpm 3 days |
| Escherichia coli | + | | |
| Escherichia coli | + | | |
| Bacillus circulans | + | | |

Sample broths from different genus and different species can be assayed for CS-like compound production. As outlined in FIG. 4, a first assay screened 2,208 sample broths from 34 different genus and 240 different species using the DMMB assay as described in Example 1. From this screen, 400 sample broths tested positive for CS-like compound production. From these 400 sample broths, sample broths from 10 different genus (*Aspergillus, Bacillus, Candida, Eschericia, Monascus, Mucor, Penicillium, Rhizomucor, Rizopus,* and *Saccharomyces*) were selected for further analysis. As shown in Table 2 below, 26 samples were analyzed for 4S:6S ratio by ELISA (as described in Example 8 below) and 19 of these samples were analyzed for CS-like compound molecular weight determination.

TABLE 2

First Screening Results for CS-Producing Microbial Strains

| Sample. | Fermentation Method | Strain Name | DMMB Assay | 4S/6S | MW (daltons) |
|---|---|---|---|---|---|
| 1 | Fungi (solid state fermentation) | Monascus purpureus | 0.110 | 0.37 | |
| 2 | Fungi (solid state fermentation) | Aspergillus oryzae BB-1-84-38 | 0.129 | 0.1 | 33,000-5400 |
| 3 | Eucarya (submerged fermentation) | Mucor javanicus | 0.139 | 6.02 | 10,000-1000 |
| 4 | Fungi (solid state fermentation) | Penicillium camembertii | 0.134 | 0.08 | 18,000-5400 |
| 5 | Eucarya (submerged fermentation) | Mucor circinelloides f. circinelloides | 0.137 | 3.08 | |
| 6 | Eucarya (submerged fermentation) | Mucor javanicus | 0.144 | 0.44 | 3000-360 |
| 7 | Eucarya (submerged fermentation) | Rhizomucor miehei | 0.073 | 0.08 | 1400-360 |
| 8 | Eucarya (submerged fermentation) | Rhizomucor miehei | 0.071 | 0.06 | 10,000-1400 |
| 9 | Fungi (solid state fermentation) | Penicillium roquefortii | 0.219 | 0.03 | 10,000-1200 |
| 10 | Eucarya (submerged fermentation) | Monascus purpureus | 0.031 | 6.19 | 1400-360 |
| 11 | Fungi (solid state fermentation) | Rhizomucor pusillus | 0.071 | 0.39 | 13,400-2200 |
| 12 | Fungi (solid state fermentation) | Penicillium funiculosum | 0.229 | 0.12 | 13,400-4000 |
| 13 | Eucarya (submerged fermentation) | Mucor javanicus | 0.147 | 0.34 | 19,000-1400 |
| 14 | Eucarya (submerged fermentation) | Rhizopus oryzae | 0.027 | 3.44 | 18,000-3000 |
| 15 | Eucarya (submerged fermentation) | Rhizopus oryzae | 0.056 | 0.15 | 24,500-4000 |
| 16 | Eucarya (submerged fermentation) | Rhizopus oryzae | 0.036 | 0.059 | 24,500-4000 |
| 17 | Eucarya (submerged fermentation) | Mucor javanicus | 0.064 | 0.22 | 18,000-4000 |
| 18 | Eucarya (submerged fermentation) | Rhizomucor pusillus | 0.079 | 0.15 | 13,400-1000 |
| 19 | Eucarya (submerged fermentation) | Rhizomucor miehei | 0.039 | 5.52 | 13,400-900 |
| 20 | Eucarya (submerged fermentation) | Monascus purpureus | 0.017 | 6.79 | 10,000-1200 |
| 21 | Bacteria (submerged fermentation) | Bacillus subtilis | 0.144 | 0.24 | |
| 22 | Bacteria (submerged fermentation) | Escherichia coli | 0.193 | | |
| 23 | Bacteria (submerged fermentation) | Escherichia coli | 0.180 | 0.66 | |
| 24 | Bacteria (submerged fermentation) | Bacillus licheniformis | 0.245 | 0.018 | |
| 25 | Bacteria (submerged fermentation) | Bacillus licheniformis 501SMN11-MCI1 | 0.205 | | 18,000-5400 |
| 26 | Bacteria (submerged fermentation) | Bacilluks circulans | 0.150 | 2.92 | |

Based on the screening described above and a second screening, 132 microbial strains were selected as CS (or CS-like compound) production strains. Tables 3-4 set forth these strains and the amount of CS (or CS-like compound) detected in their culture media (ng/mL) as derived from a standard curve using the DMMB assay. Table 3 lists bacterial strains and Table 4 lists fungal strains.

TABLE 3

CS-Producing Bacteria

| Bacterial Species | CS (ng/ml) |
|---|---|
| Bacillus cereus | 8.6 |
| Bacillus circulans | 11.7 |
| Bacillus coagulans | 8.5 |
| Bacillus licheniformis | 9.0 |
| Bacillus megaterium | 8.8 |
| Bacillus subtilis | 8.9 |
| Lactobacillus acidophilus | 8.9 |
| Corynebacterium glutamicum | 80.8 |
| Microbacterium arborescens | 8.0 |
| Micrococcus varians | 8.7 |
| Monascus purpureus | 10.1 |
| Streptomyces olivochromogenes | 8.3 |
| Streptomyces rubginosus | 8.0 |
| Escherichia coli | 8.8 |

TABLE 4

CS-Producing Fungi

| Fungal Species | CS (ng/ml) |
|---|---|
| Aspergillus repens | 8.17 |
| Aspergillus sydowi | 8.72 |
| Aspergillus aculeatus | 92.36 |
| Aspergillus faponicus | 92.68 |
| Aspergillus kawachii | 82.68 |
| Aspergillus melleus | 93.64 |
| Aspergillus nidulans | 8.18 |
| Aspergillus niger var. Intermedius | 80.28 |
| Aspergillus phoenicis | 93.88 |
| Aspergillus pulverulentus | 91.88 |
| Aspergillus sulphureus var. minimus | 86.68 |
| Aspergillus terreus | 8.18 |
| Aspergillus terricola | 90.20 |
| Aspergillus usamii | 88.84 |
| Aspergillus versicolor | 93.08 |
| Aspergillus wentii | 95.00 |
| Aspergillus aureus | 95.08 |
| Aspergillus awamori | 9.66 |
| Aspergillus candidus | 95.40 |
| Aspergillus chevalieri | 80.36 |
| Aspergillus favipes | 8.32 |

TABLE 4-continued

CS-Producing Fungi

| Fungal Species | CS (ng/ml) |
|---|---|
| Aspergillus fisheri | 8.98 |
| Aspergillus flavus | 125.96 |
| Aspergillus nakazawai | 95.16 |
| Aspergillus niger | 11.14 |
| Aspergillus oryzae | 11.10 |
| Aspergillus phoenicis | 84.52 |
| Aspergillus sojae | 8.02 |
| Aspergillus sp BB46-2-22 | 9.21 |
| Candida albicans | 11.84 |
| Candida cylindracea | 9.99 |
| Candida fermentati | 11.65 |
| Candida guilliermondii | 84.88 |
| Candida intermedia | 8.10 |
| Candida kefyr | 8.83 |
| Candida krusei | 8.74 |
| Candida maltosa | 8.34 |
| Candida mycoderma | 8.64 |
| Candida pelliculosa | 8.94 |
| Candida rugosa | 10.64 |
| Candida tenuis | 82.08 |
| Candida tropicalis | 11.50 |
| Candida utilis | 8.96 |
| Cryptococcus albidus var. Diffluens | 8.35 |
| Cryptococcus laurentii | 8.74 |
| Debariomyces hansenii | 10.11 |
| Debaryomyces kloekeri | 9.41 |
| Debaryomyces polymorphus | 82.24 |
| Dipodascus magnusii | 8.65 |
| Endomycopsella vini | 81.52 |
| Endomycopsis capsularis | 8.34 |
| Eurotium chevalieri | 82.12 |
| Galactomyces reessii | 8.87 |
| Geotrichum candidum | 81.88 |
| Hansenula carifornica | 8.66 |
| Hasegawaea japonica | 8.64 |
| Kluveromyces marxianus | 8.50 |
| Kluyveromyces fragilis | 8.15 |
| Kluyveromyces lactis | 11.56 |
| Kluyveromyces marxianus | 8.36 |
| Mortierella vinacea | 8.49 |
| Mucor circinelloides f. circinelloides | 9.10 |
| Mucor javanicus | 10.73 |
| Penicillium camembertii | 9.14 |
| Penicillium funiculosum | 8.68 |
| Penicillium lilacinum | 86.44 |
| Penicillium multicolor | 8.99 |
| Penicillium roquefortii | 8.69 |
| Pichia anomala | 9.98 |
| Pichia farinosa | 10.00 |
| Pichia membranaefaciens | 9.42 |
| Rhizomucor miehei | 8.86 |
| Rhizomucor pusillus | 8.48 |
| Rhizopus acetoinus | 82.52 |
| Rhizopus achlamydosporus | 94.20 |
| Rhizopus chinensis | 88.44 |
| Rhizopus chungkuoensis | 84.12 |
| Rhizopus chuniang | 86.76 |
| Rhizopus delemar | 88.84 |
| Rhizopus formosaensis | 88.52 |
| Rhizopus hangchow | 89.08 |
| Rhizopus jaranicus | 90.28 |
| Rhizopus kansho | 88.20 |
| Rhizopus microsporus | 85.80 |
| Rhizopus nigricans | 84.92 |
| Rhizopus niveus | 8.10 |
| Rhizopus nodosus | 89.08 |
| Rhizopus oligosporus | 8.05 |
| Rhizopus oryzae | 8.78 |
| Rhizopus peka II | 87.48 |
| Rhizopus peka I | 89.64 |
| Rhizopus pseudochinensis | 89.56 |
| Rhizopus reflexus | 85.96 |
| Rhizopus salebrosus | 87.96 |
| Rhizopus shanghaiensis | 83.08 |
| Rhizopus stolonifer | 8.05 |
| Rhizopus tamarii | 86.84 |
| Rhizopus thermosus | 86.68 |
| Rhizopus tonkinensis | 83.56 |
| Rhodotorula glutinis | 8.35 |
| Rhodotorula mucilaginosa | 8.57 |
| Saccharomyces cerevisiae | 11.50 |
| Saccharomyces delbrueckii var. Mongolicus | 9.36 |
| Saccharomyces fragilis | 8.42 |
| Saccharomyces lactis | 8.30 |
| Saccharomyces marxianus | 8.52 |
| Schizosaccharomyces pombe | 9.41 |
| Streptomyces fradiae No. 15 | 8.02 |
| Talaromyces emersonii | 8.21 |
| Torulopsis dattila | 9.90 |
| Torulopsis globosa | 8.94 |
| Trichoderma reesei | 8.28 |
| Trichoderma viride | 8.04 |
| Trichosporon cutaneum | 10.68 |
| Yamadazyma farinosa | 8.16 |
| Yamadazyma guilliermondii | 9.31 |
| Yarrowia lipolytica | 83.60 |
| Zygosaccharomyces rouxii | 8.54 |

Example 7. CS-Like Compound Production by Various *Bacillus natto* Strains

To assess production of CS-like compound across various *Bacillus natto* strains, five different strains were analyzed for microbial CS-like compound production using the methods described in Example 2. Microbial CS-like compound production was found for three strains: the Miyagino, Naruse, and Takahashi strain. Two strains, Daiwa strain 1 and Daiwa strain 2, did not produce a CS-like compound.

Figure 3A:
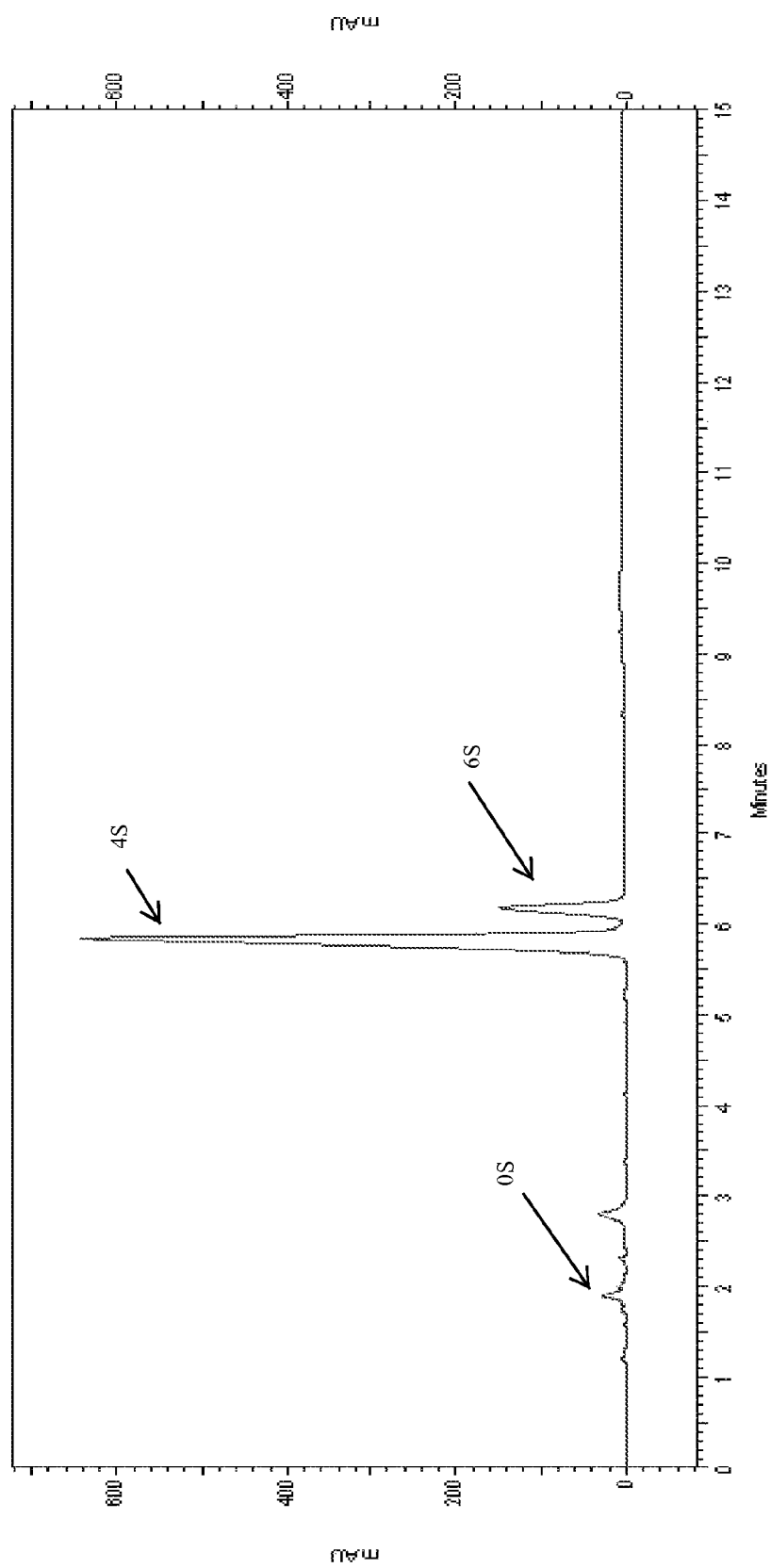
FIGS. 3A-3D show typical HPLC analysis of CS from bovine trachea (FIG. 3A), shark cartilage (FIG. 3B), porcine trachea (FIG. 3C), and *Bacillus natto* Naruse strain (FIG. 3D).
Figure 3B:
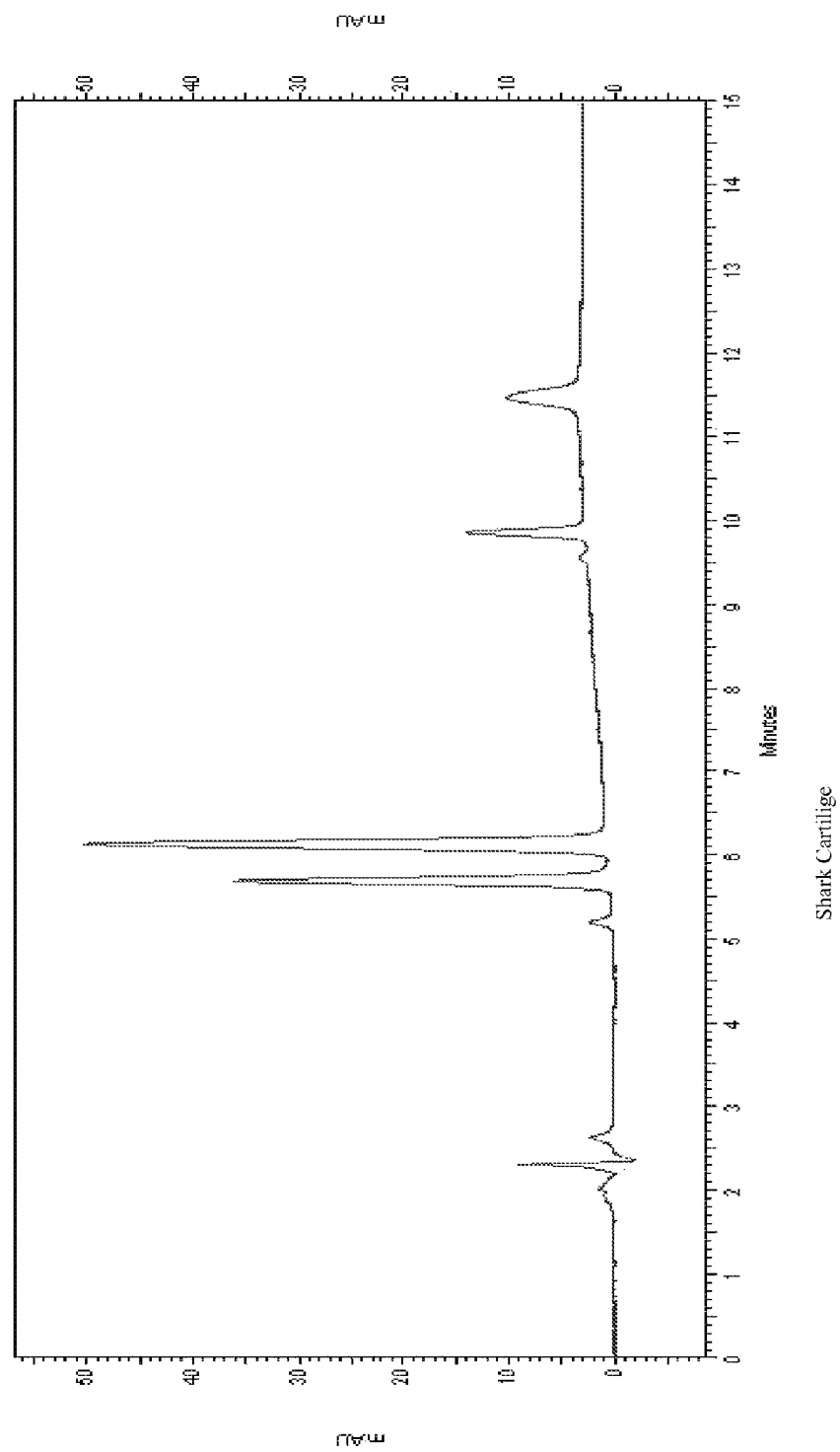
Figure 3C:
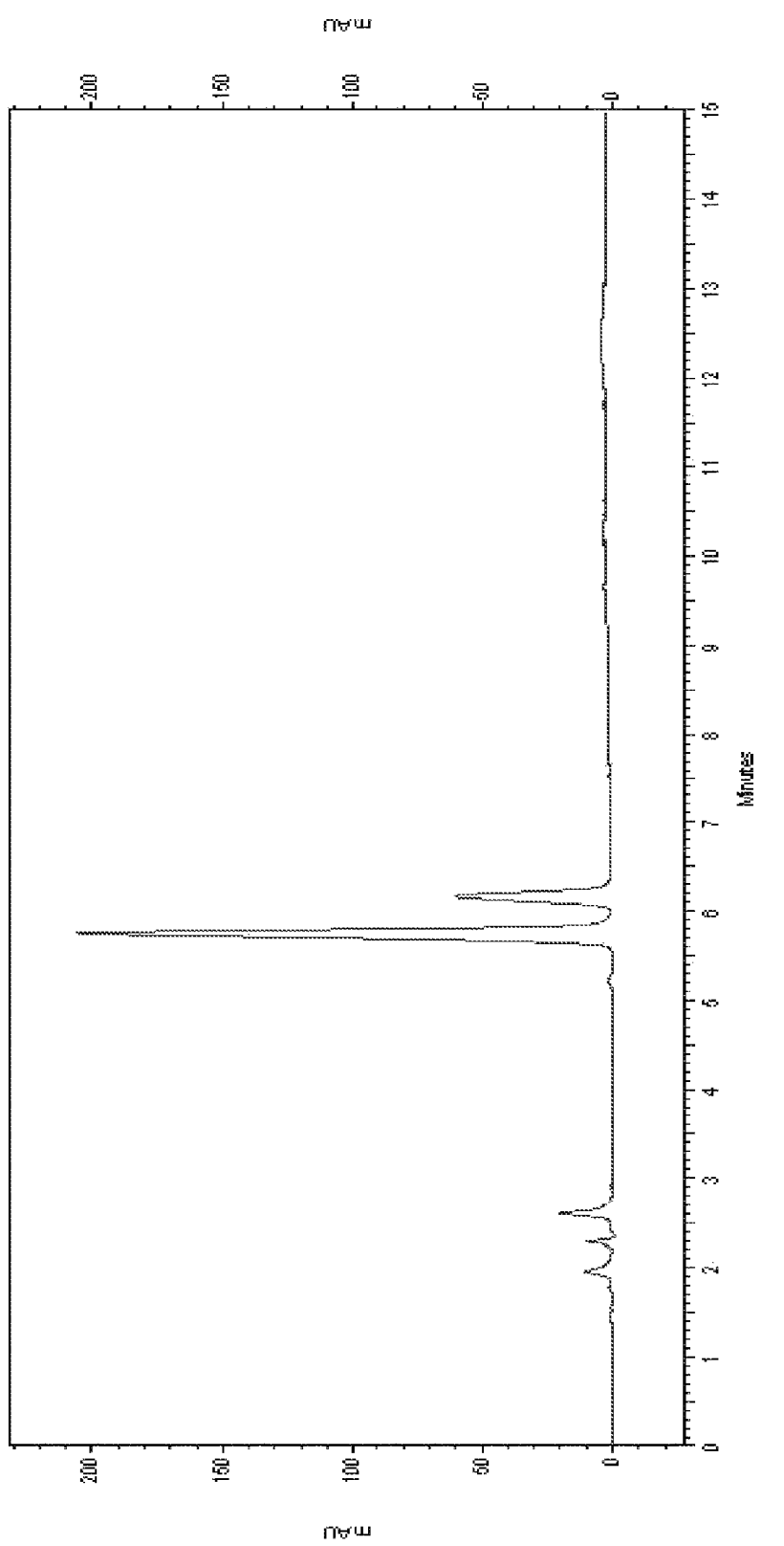
Figure 3D:
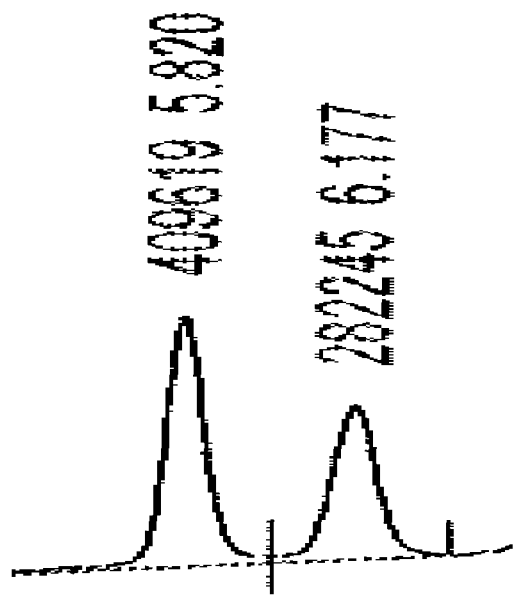

Purified Naruse CS-like compound was analyzed by HPLC as described in Example 4 and the results are shown in FIG. 3(D). Notably, the 4S peak (first peak) and the 6S peak (second peak) are of similar intensity, indicating similar amounts of 4S and 6S, which is different from animal CS (porcine or bovine or shark).

Example 8. ELISA Analysis of CS Digestion Products

CS or CS-like compound derived from bovine, *Bacillus natto* Naruse strain, and porcine (Zeria Pharmaceutical Co., Ltd. Japan) were digested with chondroitinase AC (EC 4.2.2.5) (Sigma) as described in Example 4, except the digestion products were not analyzed by HPLC. Instead, the digestion products were immobilized in a microtiter well by standard ELISA procedures and analyzed by antibodies to 4S and 6S (Millipore). The antibodies are mouse monoclonal antibodies which can be detected by anti-mouse horseradish peroxidase conjugated antibody (Sigma) and detected by fluorescence using the QuantaBlu detection kit (Thermo Fisher).

As shown in FIG. 5, the 4S/6S pattern for each CS is similar to that observed by HPLC analysis. The advantage of the ELISA method is that it can be used to characterize samples that are less concentrated and not extensively purified.

Example 9. CS-Like Compound Production by Various *Bacillus* Srains

The production of CS-like compound across various *Bacillus* strains was assessed as described in Example 2.

Microbial CS-like compound production was found for 73 strains, as illustrated in Table 5 below, which also shows the amount of CS (or CS-like compound) detected in their culture media (μg/mL) as derived from a standard curve using the DMMB assay.

TABLE 5

CS-Producing *Bacillus* Strains

| *Bacillus* Strain | CS (μg/mL) |
|---|---|
| Bacillus alvei | 62.0 |
| Bacillus amyloquefaciens | 419.8 |
| Bacillus aneurinolyticus | 62.0 |
| Bacillus atrophaeus | 9.0 |
| Bacillus brevis | 86.1 |
| Bacillus cereus BA-1 | 22.0 |
| Bacillus cereus K681 | 103.4 |
| Bacillus cereus var. mycoides | 25.0 |
| Bacillus circulans | 66.4 |
| Bacillus coagulans | 14.2 |
| Bacillus firmus | 103.4 |
| Bacillus flexus | 74.0 |
| Bacillus flexus BA2 | 77.0 |
| Bacillus fusiformis | 27.0 |
| Bacillus halodurans | 67.0 |
| Bacillus licheniformis | 94.1 |
| Bacillus licheniformis CE207 | 13.0 |
| Bacillus licheniformis CE262 | 201.0 |
| Bacillus megaterium GDH-1 | 46.0 |
| Bacillus megaterium No. 3344 | 52.0 |
| Bacillus mycoides | 30.0 |
| Bacillus polymyxa | 1.0 |
| Bacillus polymyxa EH-4 | 3.0 |
| Bacillus pumilus | 117.0 |
| Bacillus racemilacticus | 89.0 |
| Bacillus roseus | 78.1 |
| Bacillus sp. | 100.0 |
| Bacillus sp. A-15 | 74.0 |
| Bacillus sp. A-3 | 71.0 |
| Bacillus sp. CE-207-1 | 12.0 |
| Bacillus sp. CE-207-4 | 15.0 |
| Bacillus sp. CE-262-7 | 250.0 |
| Bacillus sp. CE-262-C | 244.0 |
| Bacillus sp. L1HT1 | 73.0 |
| Bacillus sp. No. 128 | 18.0 |
| Bacillus sp. No. 56Y001DA011-4 | 27.0 |
| Bacillus sp. No. 71Y001DA023-01 | 9.0 |
| Bacillus sp. Origin 34 | 80.0 |
| Bacillus sp. Origin 6 | 85.0 |
| Bacillus sphaericus | 90.0 |
| Bacillus sphaericus | 19.0 |
| Bacillus stearothermophilus | 30.4 |
| Bacillus subtilis | 103.0 |
| Bacillus subtilis (natto sawamura) | 89.6 |
| Bacillus subtilis (natto) | 237.7 |
| Bacillus subtilis A-1 | 83.0 |
| Bacillus subtilis A-10 | 79.0 |
| Bacillus subtilis A-11 | 73.0 |
| Bacillus subtilis A-12 | 97.0 |
| Bacillus subtilis A-13 | 77.0 |
| Bacillus subtilis A-14 | 111.0 |
| Bacillus subtilis A-2 | 114.0 |
| Bacillus subtilis A-3 | 95.0 |
| Bacillus subtilis A-4 | 80.0 |
| Bacillus subtilis A-5 | 104.0 |
| Bacillus subtilis A-6 | 103.0 |
| Bacillus subtilis A-7 | 143.0 |
| Bacillus subtilis A-8 | 82.0 |
| Bacillus subtilis A-9 | 91.0 |
| Bacillus subtilis K wild | 86.1 |
| Bacillus subtilis Marburg W23 SM | 215.9 |
| Bacillus subtilis naruse | 171.3 |
| Bacillus subtilis R1 | 109.0 |
| Bacillus subtilis R2 | 128.0 |
| Bacillus subtilis S3 | 164.0 |
| Bacillus subtilis subsp. subtilis | 94.0 |
| Bacillus subtilis var. atterimus | 799.5 |
| Bacillus subtilis var. niger | 137.8 |
| Bacillus thermoamyloliquefaciens | 11.5 |
| Bacillus thermodenitrificans | 12.2 |
| Bacillus thermoproteolyticus BT-9 | 31.8 |
| Bacillus thuringiensis | 22.0 |
| Bacillus natto | 100.0 |

What is claimed is:

1. A method for producing chondroitin sulfate, comprising
   (a) incubating a microbial culture comprising a fungus in culture medium at a culturing temperature of from about 10° C. to about 50° C. to obtain a culture medium comprising chondroitin sulfate; and
   (b) purifying said culture medium to obtain chondroitin sulfate, wherein said purifying comprises a method selected from the group consisting of centrifugation of said culture medium to remove microbial cells from said culture medium, filtration of said culture medium, chromatography of said culture medium, and alcohol precipitation of said culture medium.

2. The method of claim 1, wherein said fungus comprises a naturally occurring fungus.

3. The method of claim 2, wherein said fungus is from a genus selected from the group consisting of *Aspergillus, Endomycopsella, Endomycopsis, Hansenula, Hasegawaea, Penicillium, Pichia, Monascus, Candida, Debaryomyces, Eurotium, Galactomycetes, Geotrichum, Rhodotorula, Saccharomyces, Trichoderma, Kluveromyces, Schizosaccharomyces, Streptomyces, Talaromyces, Torulopsis, Yamadazyma, Yarrowia, Zygosaccharomyces, Mucor, Mortierella, Rhizomucor, Rhizopus, Cryptococcus, Dipodascus*, and *Trichosporon*.

4. The method of claim 1, wherein said incubating comprises incubating said microbial culture in culture medium comprising nutrient broth at 37° C.

5. The method of claim 1, wherein said incubating comprises incubating said microbial culture in culture medium at 30° C.

6. The method of claim 1, wherein said incubating comprises two stages, comprising a first stage comprising incubating in a pre-culture medium and a second stage comprising incubating in a main culture medium.

* * * * *